US005460834A

United States Patent [19]

Bhagat

[11] Patent Number: 5,460,834
[45] Date of Patent: Oct. 24, 1995

[54] COMBINATIONS OF POLYMERS FOR USE IN PHYSIOLOGICAL TEAR COMPOSITIONS

[75] Inventor: Haresh G. Bhagat, Fort Worth, Tex.

[73] Assignee: Alcon Laboratories, Inc., Fort Worth, Tex.

[21] Appl. No.: 371,043

[22] Filed: Jan. 10, 1995

Related U.S. Application Data

[63] Continuation of Ser. No. 170,482, Dec. 20, 1993, abandoned, and a continuation-in-part of Ser. No. 994,051, Dec. 16, 1992, abandoned, which is a continuation of Ser. No. 807,528, Dec. 13, 1991, abandoned, said Ser. No. 170,482, is a continuation-in-part of Ser. No. 31,058, Mar. 12, 1993, abandoned, which is a continuation of Ser. No. 844,269, Mar. 2, 1992, abandoned.

[51] Int. Cl.$^6$ .......................... A61K 33/06; A61K 33/00; A61K 47/00
[52] U.S. Cl. ..................... 424/682; 424/717; 514/781; 514/912
[58] Field of Search .................................. 424/682, 717; 514/781, 912

[56] References Cited

U.S. PATENT DOCUMENTS

| | | | |
|---|---|---|---|
| 3,920,810 | 11/1975 | Rankin | 424/80 |
| 4,039,662 | 8/1977 | Hecht et al. | 424/180 |
| 4,371,522 | 2/1983 | Gilbard | 424/153 |
| 4,443,432 | 4/1984 | Garabedian et al. | 424/127 |
| 4,550,022 | 10/1985 | Garabedian et al. | 424/127 |
| 4,775,531 | 10/1988 | Gilbard | 424/128 |
| 4,917,271 | 4/1990 | Kanner et al. | 222/189 |
| 5,025,957 | 6/1991 | Ranalletta et al. | 222/189 |
| 5,075,104 | 12/1991 | Gressel et al. | 424/78.04 |
| 5,209,927 | 5/1993 | Gressel et al. | 424/78.04 |

FOREIGN PATENT DOCUMENTS

| | | |
|---|---|---|
| 0205279A1 | 12/1986 | European Pat. Off. . |
| 0286791A1 | 10/1988 | European Pat. Off. . |
| 0546728A2 | 12/1991 | European Pat. Off. . |
| 3440352A1 | 5/1986 | Germany . |
| WO91/19481 | 12/1991 | WIPO . |

OTHER PUBLICATIONS

Bachman et al., "Essential Ions for Maintenance of the Corneal Epithelial Surface," *Investigative Ophthalmology & Visual Science*, 26:1484–1488 (1985).
"Carbopol® Water Soluble Resins," B. F. Goodrich Technical Bulletin, pp. 4–6 (1987).
*Chemical & Engineering News*, Sept. 29, 1958, pp. 64–65.
Bernal, D. L. and J. L. Ubels, "Quantitative Evaluation of the Corneal Epithelial Barrier: Effect of Artificial Tears and Preservatives," *Curr. Eye Res.*, 10(7):645–656 (1991).
Doughty, M. J., "Evidence for a Direct Effect of Bicarbonate on the Rabbit Corneal Stroma," *Optometry & Vision Sci.*, 68(9):687–698 (1989).
*Drug Facts and Comparisons*, New York: J. B. Lippincott Co., 1989, pp. 504–504b.
Edelhauser, H. et al., "Intraocular Irrigating Solution," *Arch. Ophthal.*, 93:648–657 (1975).
Glasser, et al., Chapter 17 of *The Cornea: Trans. of the World Congress on the Cornea III* H. D. Cavanagh, ed.), New York: Raven Press Ltd., 1988.
Meltzer, *Water-Soluble Polymers, Developments Since 1978*, Noyes Data Corp.:Park Ridge, N.J. (1981), pp. 130–167.
Rismondo, V. et al., "Electrolyte Composition of Lacrimal Gland Fluid and Tears of Normal and Vitamin A–Deficient Rabbits," *CLAO Journal*, 15(3):222–229 (1989).

*Primary Examiner*—Zohreh Fay
*Attorney, Agent, or Firm*—Jeffrey S. Schira

[57] ABSTRACT

The use of physiological tear compositions for the treatment of dry eye syndrome. The compositions have a high viscosity and contain bicarbonate, at least one cellulosic polymer and at least one carboxy vinyl polymer.

18 Claims, No Drawings

COMBINATIONS OF POLYMERS FOR USE IN PHYSIOLOGICAL TEAR COMPOSITIONS

This application is a continuation of application Ser. No. 08/170,482, filed Dec. 20, 1993, now abandoned, which is a continuation-in-part application of U.S. patent application Ser. No. 08/031,058, filed Mar. 12, 1993, now abandoned which is a continuation of U.S. patent application Ser. No. 07/844,269, filed Mar. 2, 1992, now abandoned. This application is also a continuation-in-part application of U.S. patent application Ser. No. 07/994,051, filed Dec. 16, 1992, now abandoned, which is a continuation of U.S. patent application Ser. No. 07/807,528, filed Dec. 13, 1991, now abandoned.

Background of the Invention

This invention relates generally to ophthalmic compositions. In particular, the present invention relates to artificial tear compositions comprising the ionic components of normal human tear film in substantially the same amounts and proportions, as well as to methods for their preparation and storage. These compositions are useful as lubricating and cushioning agents for the eye after traumatic injury or surgery. The present invention also relates to a method of treating eyes by topically applying the compositions of the present invention when indicated for the relief of dry eye syndrome and when indicated to achieve the other effects mentioned above.

Dry eye syndrome and related ailments, including transitory discomforts, are well known in the scientific and patent literature. These ailments have generally been treated by topical administration of any of a number of ophthalmic compositions. The currently marketed artificial tear compositions are listed on pages 504–504b of *Drug Facts and Comparisons*, New York: J. B. Lippincott Co., 1989. In general, these compositions contain salts, buffers and viscosity agents (e.g., hydroxypropyl methylcellulose, polyvinyl alcohol or Carbopol®, a carboxy vinyl polymer). Most artificial tear compositions additionally contain preservatives (e.g., benzalkonium chloride, Dymed®, a biguanide, and Polyquad®, a polymeric quaternary ammonium compound), although some recently introduced compositions are non-preserved.

It has recently been determined that preservatives and non-physiologic ions which may be present in artificial tear compositions may be detrimental to the corneal epithelium. See, for example, Bernal et al., *Current Eye Research*, 10(7):645–656 (1991). There have therefore been attempts to develop nonpreserved artificial tear compositions containing physiological tear components. See, for example, U.S. Pat. No. 4,775,531 (Gilbard); however, these formulations are based on the composition of rabbit tears and it has now been documented that human tears, although having the same types of ions, have distinctly different ion concentrations. See Rismondo et al., in *The Contact Lens Association of Ophthalmologists*, 15(3):222–229 (1989). In addition, although Gilbard's compositions list bicarbonate as an ingredient, bicarbonate is quite labile because it is in equilibrium with carbon dioxide, and can escape from solution in a relatively short time.

SUMMARY OF THE INVENTION

The compositions of the present invention are non-preserved compositions which contain the essential ionic components of normal human tear film in substantially the same amounts and proportions and which avoid some of the problems of known compositions. In addition, it has surprisingly been found that compositions containing bicarbonate are substantially more effective in treating dry eye syndrome and its related ailments, than currently available artificial tear preparations.

Additionally, the present invention is based on the finding that compositions comprising certain combinations of at least one cellulosic polymer and at least one carboxy vinyl polymer are much more viscous than similar compositions containing only one type of polymer. That is, a lower polymer concentration is required to achieve a higher viscosity when polymer combinations of the present invention are used than when only one of the polymers is used. This is particularly beneficial in the ophthalmic field, because a reduction in the overall polymer concentration in an ophthalmic composition generally results in greater patient comfort. Using the polymer combinations of the present invention, higher viscosity can be achieved without increasing the overall polymer concentration. This high viscosity aids in the retention of the composition in the eye and permits the maintenance of the moisturizing effect, of particular importance with respect to artificial tear formulations.

Further, the compositions of the present invention are prepared by an unique method which involves the use of $CO_2$ gas in order to retain bicarbonate in solution during preparation. The amount of bicarbonate dissolved in the solution depends on the components and conditions in the solution, as well as the conditions of the atmosphere surrounding the solution. An equilibrium is established which depends on these parameters, as described in the equation below:

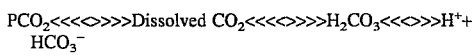

(where $PCO_2$ is the partial pressure of $CO_2$ above the solution). The bicarbonate concentration is maintained during storage by use of the novel packaging of the present invention, which creates a closed system in which an equilibrium between $CO_2$ and bicarbonate can be reached and maintained until the composition is to be used.

DETAILED DESCRIPTION OF THE INVENTION

In general, the physiological tear compositions of the present invention comprise the following ion components: potassium at a concentration of between about 11 and about 25 millimoles per liter (mmol/L); calcium at a concentration of between about 0.2 and about 0.5 mmol/L; magnesium at a concentration of between about 0.15 and about 0.45 mmol/L; and bicarbonate at a concentration of between about 1 and about 36 mmol/L, preferably between about 6 and about 24 mmol/L. The compositions may additionally contain zinc at a concentration between about 0.005 and about 0.015 mmol/L. In a preferred composition, the potassium ion concentration is about 17.4 mmol/L, the calcium ion concentration is about 0.36 mmol/L, the magnesium ion concentration is about 0.31 mmol/L and the bicarbonate concentration is about 11.9 mmol/L. As used throughout this application, all concentrations refer to final composition concentrations, unless otherwise stated.

These physiological tear compositions preferably have certain ion ratios. In particular, it is preferred that: the molar concentration ratio of potassium to bicarbonate is between about 1:0.04 and about 1:3.27; the molar concentration ratio of calcium to magnesium is between about 1:0.3 and about 1:2.25; the molar concentration ratio of potassium to calcium is between about 1:0.008 and about 1:0.045; and the molar concentration ratio of bicarbonate to calcium is between about 1:0.0056 and about 1:0.5. Especially preferred are molar concentration ratios off potassium to bicarbonate between about 1:0.24 and about 1:2.18; and bicarbonate to calcium between about 1:0.008 and about 1:0.08. Most preferred are the compositions wherein the molar concentration ratio of potassium to bicarbonate is about 1:0.68, the molar concentration ratio calcium to magnesium is about 1:0.86, the molar concentration ratio of potassium to calcium is about 1:0.02 and the molar concentration ratio of bicarbonate to calcium is about 1:0.03.

The compositions of the present invention further comprise a combination of at least two types of polymers selected from the group consisting of: cellulosic polymers, glycosaminoglycans, and carboxy vinyl polymers. These viscous compositions will generally have a viscosity between about 5 and 15,000 centipoise (cps), preferably between about 2,000 and 10,000 cps, and most preferably between about 3,000 and about 6,000 cps. The viscosity of such compositions will vary, depending on the particular polymer combinations used and the relative concentrations of each polymer.

The cellulosic polymers useful in the viscous compositions of the present invention include all cellulose derivatives which exhibit viscoelastic properties. In general, such cellulosic polymers have an average molecular weight between about 10,000 and 13 million. Preferred cellulosic polymers include: hydroxypropyl methyl cellulose (HPMC), hydroxyethyl cellulose (HEC), hydroxypropyl cellulose (HPC) and methyl cellulose (MC). In general, these cellulosic polymers are present in the compositions of the present invention at a concentration between about 0.05 and about 5.0 percent by weight (wt %), preferably between about 0.25 and about 1.0 wt %, and most preferably at about 0.5% wt %.

The glycosaminoglycans (GAGs) useful in the viscous compositions of the present invention include chondroitin sulfate (COS), hyaluronic acid (HA), and keratan sulfate. These GAGs have average molecular weights between about 25,000 and about 2,000,000. In general, the GAGs are present in the compositions of the present invention at a concentration between about 0.1 and about 10.0 wt %, preferably between about 0.2 and about 5.0 wt %.

The carboxy vinyl polymers useful in the viscous compositions of the present invention have an average molecular weight between about 500,000 and 6 million. The polymers are characterized as having carboxylic acid functional groups and preferably contain between 2 and 7 carbon atoms per functional group. Suitable carboxy vinyl polymers include those called carbomers, e.g., Carbopol® (B. F. Goodrich Co., Cleveland, Ohio). Specifically preferred are: carbomer 910, carbomer 940, carbomer 934P, carbomer 947P, carbomer 980 and carbomer 1342. Carbomer 934P and carbomer 974P are the most preferred. Such polymers will typically be employed in an amount between about 0.05 and about 3.0 wt %, depending on the desired viscosity of the composition. Preferably, the carboxy vinyl polymer is present at a concentration between abut 0.1 and about 0.5 wt %, and most preferably at a concentration of about 0.175%.

The preferred compositions of the present invention are viscous, physiological tear compositions which include the ion components and the viscosity enhancing polymer combinations detailed above.

The compositions of the present invention may contain one or more pharmaceutically active agents ("actives"). Such actives include, but are not limited to: glaucoma agents, such as miotics (e.g., pilocarpine, carbachol and acetylcholinesterase inhibitors), sympathomimetics (e.g., epinephrine, dipivalylepinephrine and para-amino clonidine), beta-blockers (e.g., betaxolol, levobunolol and timolol) and carbonic anhydrase inhibitors (e.g., acetazolamide, methazolamide and ethoxzolamide); dopaminergic antagonists; antihypertensive agents, such as para-amino clonidine (also known as apraclonidine); anti-infectives, such as ciprofloxacin; non-steroidal and steroidal anti-inflammatories, such as suprofen, ketorolac, tetrahydrocortisol, dexamethasone, diclofenac and rimexolone; prostaglandins; retinoids; aldose reductase inhibitors; proteins; growth factors, such as epidermal growth factor; and anti-allergics.

The compositions of the present invention may contain sodium chloride at a concentration between about 75 and about 154 mmol/L so that the osmolality is between about 200 and about 350 millimoles/kilogram (mOsm/kg). It is preferred that the compositions have an osmolality of between about 260 and about 330 mOsm/kg. The compositions of the present invention will have a pH between about 5.0 and about 9.5. It is preferred that the compositions have a pH between about 5.5 and 8.5.

The compositions of the present invention additionally may contain mucomimetic polymers and lubricating agents for increased comfort and sustained duration in the eye. Examples of the above include: Dextran; polyvinyl pyrrolidone; and polyethylene glycols. In general, these polymers are present in the compositions of the present invention at a concentration between about 0.05 and about 5.0 percent by weight (wt %), preferably between about 0.1 and about 2.0 wt %.

The compositions of the present invention may be prepared by dissolving or dispersing all of the ingredients in purified water in a pressure vessel. The components are mixed and the reactor heated to a suitable temperature for a time sufficient to achieve assured sterilization, according to common sterilization procedures. The mixture is then cooled to room temperature with mixing. In the alternative, a solution of bicarbonate which has previously been sterilized by filtration may be added at this stage. The pH of the composition is adjusted to the desired range (between 5.6 and 7.9) by use of sterile carbon dioxide and mixing the contents of the reactor. Sodium hydroxide and/or hydrochloric acid may additionally be used to adjust the pH of the mixture. The final product is then aseptically filled according to procedures known in the art. In another alternative, all of the ingredients are dissolved or dispersed in purified water, followed by pH adjustment as described above. Sterilization may be accomplished either by filtration of the composition into a pressure vessel prior to the pH adjustment or by filtration of the composition directly into the filling machine after pH adjustment.

The packaging for the compositions of the present invention preferably are made from a material that is relatively impermeable with respect to the gas contained in the composition. For example, if the gas is carbon dioxide, laminated foil or some high density plastics are suitable packaging materials. The final packaging may consist of multiple layers of packaging. The choice of material will in part depend on the desired product shelf life; i.e., the longer the desired shelf life, the more impermeable the material needs to be. The compositions of the present invention containing bicarbonate are preferably packaged in unit dose containers which are then sealed into laminated foil pouches. The manufacture and filling of such unit dose containers are known in the art (generally referred to as "form, fill and seal"). Multiple unit dose containers may be packaged in each laminated foil pouch.

Although it is preferred that the compositions of the present invention containing bicarbonate be packaged in unit dose containers, it is understood that multidose non-preserved dispensing package systems could be used, so long as the packaging contains an appropriate barrier to prevent or reduce the escape of gas. For example, a packaging system consisting of laminate tubes using dispensing tip assemblies such as those disclosed in U.S. Pat. No. 4,917,271 (Kanner, et al.) and U.S. Pat. No. 5,025,957 (Ranalletta, et al.), is suitable for the compositions of the present invention.

Sample formulations of the compositions of the present invention are listed in Table 1 below:

TABLE 1

| Ingredients | % W/W | | | | | | | | |
|---|---|---|---|---|---|---|---|---|---|
| Dextran | — | — | 0.1 | 0.1 | — | — | — | — | — |
| Hydroxypropyl Methyl Cellulose | 0.5 | — | 0.5 | 0.3 | 0.3 | 0.5 | 0.25 | 1.0 | 1.0 |
| Sodium Chloride* | — | — | QS | QS | QS | — | — | — | QS |
| Mannitol* | QS | QS | — | — | — | QS | QS | QS | — |
| Potassium Chloride | — | — | 0.13 | 0.13 | 0.13 | — | — | — | 0.13 |
| Calcium Chloride.2H$_2$O | — | — | 0.0053 | 0.0053 | 0.0053 | 0.0053 | 00.53 | 0.0053 | 0.0053 |
| Magnesium Chloride.6H$_2$O | — | — | 0.0064 | 0.0064 | 0.0064 | 0.0064 | 0.0064 | 0.0064 | 0.0064 |
| Zinc Chloride | — | — | 0.00015 | 0.00015 | 0.00015 | 0.00015 | 0.00015 | 0.00015 | 0.00015 |
| Sodium bicarbonate | — | — | 0.1 | 0.1 | 0.1 | — | — | — | 0.1 |
| Potassium bicarbonate | — | — | — | — | — | 0.1 | 0.1 | 0.1 | — |
| Carbomer 934P | 0.175 | 0.175 | 0.175 | — | — | 0.175 | 0.175 | — | — |
| Chondroitin Sulfate | — | — | — | 3.0 | 3.0 | — | — | — | — |
| Carboxymethyl Cellulose | — | — | — | — | — | — | — | — | — |
| Hydroxy Ethylcellulose | — | 0.75 | — | — | — | — | — | — | — |
| Hydroxypropyl Cellulose | — | — | — | — | — | — | — | — | — |
| Sodium Hyaluronate | — | — | — | — | — | — | — | — | — |
| Carbon dioxide and/or NaOH and/or HCl | QS to pH | QS to pH | QS to pH | QS to pH | QS to pH | QS to pH | QS to pH | QS to pH | QS to pH |
| Purified Water QS to | 100 | 100 | 100 | 100 | 100 | 100 | 100 | 100 | 100 |

| Ingredients | % W/W | | | | | | | |
|---|---|---|---|---|---|---|---|---|
| Dextran | — | — | 0.1 | 0.1 | — | — | — | — |
| Hydroxypropyl Methyl Cellulose | 1.0 | 1.0 | 1.0 | 0.3 | 0.5 | 0.5 | — | — |
| Sodium Chloride* | QS | QS | QS | QS | QS | QS | QS | QS |
| Mannitol* | — | — | — | — | — | — | — | — |
| Potassium Chloride | 0.13 | 0.13 | 0.13 | 0.13 | 0.13 | 0.13 | 0.13 | 0.13 |
| Calcium Chloride.2H$_2$O | 0.0053 | 0.0053 | 0.0053 | 0.0053 | 0.0053 | 0.0053 | 0.0053 | 0.0053 |
| Magnesium Chloride.6H$_2$O | 0.0064 | 0.0064 | 0.0064 | 0.0064 | 0.0064 | 0.0064 | 0.0064 | 0.0064 |
| Zinc Chloride | 0.00015 | 0.00015 | 0.00015 | 0.00015 | 0.00015 | 0.00015 | 0.00015 | 0.00015 |
| Sodium bicarbonate | 0.1 | 0.1 | 0.1 | 0.1 | 0.1 | 0.1 | 0.1 | 0.1 |
| Potassium bicarbonate | — | — | — | — | — | — | — | — |
| Carbomer 934P | — | 0.175 | — | — | — | — | — | — |
| Chondroitin Sulfate | 3.0 | — | 3.0 | — | — | — | — | 3.0 |
| Carboxymethyl Cellulose | — | — | — | — | — | — | 1.0 | 1.0 |
| Hydroxy Ethylcellulose | — | — | — | — | — | — | — | — |
| Hydroxypropyl Cellulose | — | — | — | — | — | 0.5 | — | — |
| Sodium Hyaluronate | — | — | — | 0.1 | 0.1 | — | — | — |
| Carbon dioxide and/or NaOH and/or HCl | QS to pH | QS to pH | QS to pH | QS to pH | QS to pH | QS to pH | QS to pH | QS to pH |
| Purified Water QS to | 100 | 100 | 100 | 100 | 100 | 100 | 100 | 100 |

*QS to adjust osmolality

The invention has been described by reference to certain preferred embodiments; however, it should be understood that the invention may be embodied in other specific forms or variations without departing from its spirit or essential characteristics. The embodiments described above are therefore considered to be illustrative in all respects and not restrictive, the scope of the invention being indicated by the appended claims rather than by the foregoing description.

I claim:

1. A method of manufacturing an ophthalmic composition comprising:
   a) potassium ions at a concentration between about 11 and about 25 mmol/L;
   b) calcium ions at a concentration between about 0.2 and about 0.5 mmol/L;
   c) magnesium ions at a concentration between about 0.15 and about 0.45 mmol/L;
   d) bicarbonate ions at a concentration between about 1 and about 36 mmol/L;
   e) at least one component from a group consisting of i) a cellulosic polymer ii) a glycosaminoglycan iii) a carboxy vinyl polymer; and
   f) a viscosity between about 5 and about 10,000 centipoise;
   wherein the composition is prepared by the following steps:
   i) mixing the composition ingredients in a suitable vessel;
   ii) placing the composition in a pressure reactor vessel;
   iii) charging the pressure reactor vessel with a quantity of $CO_2$ gas, wherein the quantity of the gas is sufficient to induce a desired equilibrium state between the gas and the bicarbonate within the closed system of the pressure reactor vessel; and iv) mixing the contents of the pressure reactor vessel for a period of time sufficient to induce the equilibrium state between the gas and the bicarbonate.

2. The composition of claim 1, wherein the bicarbonate ion concentration is between 6 and 24 mmol/L.

3. The composition of claim 1, further comprising zinc ions at a concentration between about 0.005 and about 0.015 mmol/L.

4. The composition of claim 1, wherein the potassium ion concentration is about 17.4 mmol/L, the calcium concentration is about 0.36 mmol/L, the magnesium ion concentration is about 0.31 mmol/L and the bicarbonate concentration is about 11.9 mmol/L.

5. The composition of claim 1, wherein:
   a) the molar concentration ratio of potassium to bicarbonate is between about 1:0.04 and about 1:3.27;
   b) the molar concentration ratio of calcium to magnesium is between about 1:0.3 and about 1:2.25;
   c) the molar concentration ratio of potassium to calcium is between about 1:0.008 and about 1:0.045; and
   d) the molar concentration ratio of bicarbonate to calcium is between about 1:0.0056 and about 1:0.5.

6. The composition of claim 5, wherein the molar concentration ratio of potassium to bicarbonate is about 1:0.68, the molar concentration ratio calcium to magnesium is about 1:0.86, the molar concentration ratio of potassium to calcium is about 1:0.02 and the molar concentration ratio of bicarbonate to calcium is about 1:0.03.

7. The composition of claim 5, wherein:
   a) the molar concentration ratio of potassium to bicarbonate is between about 1:0.24 and about 1:2.18; and
   b) the molar concentration ratio of bicarbonate to calcium is between about 1:0.008 and about 1:0.08.

8. The composition of claim 1, wherein the suitable vessel for mixing the composition ingredients is the pressure reactor vessel.

9. The composition of claim 1, further comprising transferring the contents of the pressure reactor vessel into a container without significant loss of the bicarbonate.

10. The composition of claim 1, wherein the container is substantially impermeable to the gas contained therein.

11. The composition of claim 10, wherein the container comprises a laminated foil pouch.

12. The composition of claim 1, wherein the composition has a viscosity between about 3,000 and about 6,000 centipoise.

13. The composition of claim 1, wherein the cellulosic polymer is selected from the group consisting of: hydroxypropyl methyl cellulose, hydroxyethyl cellulose, hydroxy propyl cellulose and methyl cellulose.

14. The composition of claim 1, wherein the carboxy vinyl polymer is selected from the group consisting of: carbomer 910, carbomer 940, carbomer 934P carbomer 947P, carbomer 980 and carbomer 1342.

15. The composition of claim 1, wherein the cellulosic polymer comprises hydroxypropyl methyl cellulose and the carboxy vinyl polymer comprises carbomer 934P.

16. The composition of claim 1, wherein the cellulosic polymer is present at a concentration of about 0.5 percent by weight.

17. The composition of claim 1, wherein the carboxy vinyl polymer is present at a concentration of about 0.175 percent by weight.

18. The composition of claim 1, wherein the glycosaminoglycan is present in the composition at a concentration between about 0.1 and 5 percent by weight.

* * * * *

UNITED STATES PATENT AND TRADEMARK OFFICE
CERTIFICATE OF CORRECTION

PATENT NO. : 5,460,834
DATED : October 24, 1995
INVENTOR(S) : Haresch G. Bhagat

It is certified that error appears in the above-identified patent and that said Letters Patent is hereby corrected as shown below:

Column 7, line 4: delete "composition" and insert —method—
Column 7, line 6: delete "composition" and insert —method—
Column 7, line 9: delete "composition" and insert —method—
Column 7, line 14: delete "composition" and insert —method—
Column 7, line 23: delete "composition" and insert —method—
Column 7, line 29: delete "composition" and insert —method—
Column 8, line 1: delete "composition" and insert —method—
Column 8, line 4: delete "composition" and insert —method—
Column 8, line 7: delete "composition" and insert —method—
Column 8, line 9: delete "composition" and insert —method—
Column 8, line 11: delete "composition" and insert —method—
Column 8, line 14: delete "composition" and insert —method—
Column 8, line 18: delete "composition" and insert —method—
Column 8, line 22: delete "composition" and insert —method—
Column 8, line 25: delete "composition" and insert —method—
Column 8, line 28: delete "composition" and insert —method—
Column 8, line 31: delete "composition" and insert —method—

Signed and Sealed this

Ninth Day of April, 1996

Attest:

BRUCE LEHMAN

Attesting Officer

Commissioner of Patents and Trademarks